United States Patent [19]

Tatar

[11] Patent Number: 5,228,443
[45] Date of Patent: Jul. 20, 1993

[54] METHOD FOR ESTIMATION AND DISPLAY OF CURRENT SOURCE DISTRIBUTION FROM ELECTRIC AND MAGNETIC MEASUREMENTS AND 3D ANATOMICAL DATA

[75] Inventor: Robert C. Tatar, Ballston Lake, N.Y.

[73] Assignee: General Electric Company, Schenectady, N.Y.

[21] Appl. No.: 858,786

[22] Filed: Mar. 27, 1992

[51] Int. Cl.$^5$ .................................................. A61B 5/04
[52] U.S. Cl. .............................. 128/653.2; 128/653.1; 128/731
[58] Field of Search ............... 128/653.1, 653.2, 653.5, 128/731; 364/413.13–413.16

[56] References Cited

U.S. PATENT DOCUMENTS

| | | | |
|---|---|---|---|
| 4,841,983 | 6/1989 | Duffy | 128/731 |
| 4,913,152 | 4/1990 | Ko et al. | 128/653.1 |
| 4,949,725 | 8/1990 | Raviv et al. | 128/731 |
| 4,957,116 | 9/1990 | Pernier et al. | 128/731 |
| 5,078,141 | 1/1992 | Suzuki et al. | 128/653.2 |
| 5,152,288 | 10/1992 | Hoenig et al. | 128/653.1 |

Primary Examiner—Francis Jaworski
Attorney, Agent, or Firm—Paul R. Webb, II

[57] ABSTRACT

A method for estimation and display of current source distribution within a living creature utilizes magnetic measurements taken outside of the living creature combined with 3D anatomical data generated from any procedure, such as MRI or CT scanning, which generates this type of anatomical data. The method is a modified minimum norm technique whereby the solution is limited to areas of the living creature where the electric source is expected.

3 Claims, 1 Drawing Sheet

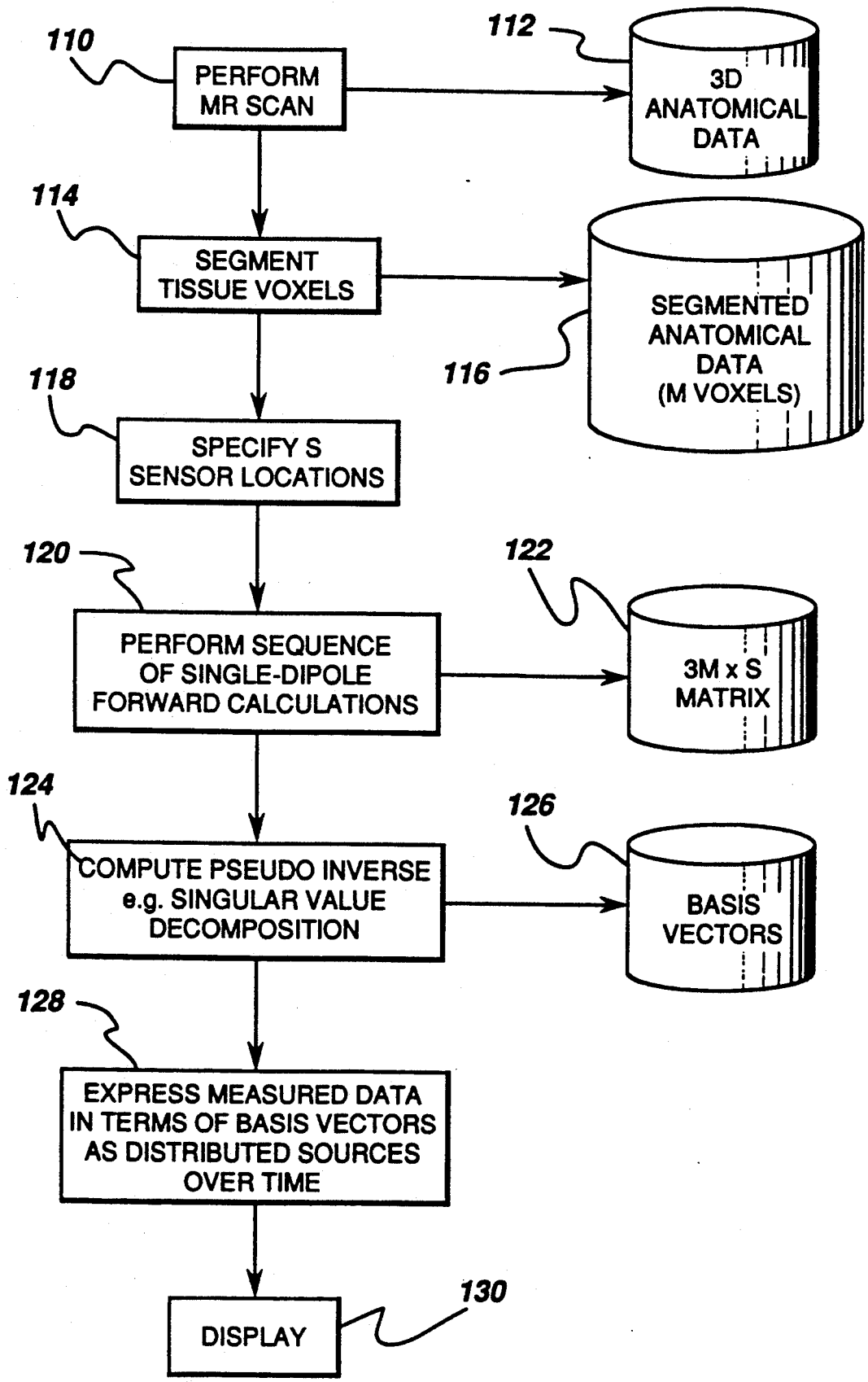

METHOD FOR ESTIMATION AND DISPLAY OF CURRENT SOURCE DISTRIBUTION FROM ELECTRIC AND MAGNETIC MEASUREMENTS AND 3D ANATOMICAL DATA

BACKGROUND OF THE INVENTION

Instrumentation has recently evolved which can measure the extremely weak, time varying magnetic fields outside the human body. These magnetic fields have been shown to be generated by electrical sources within the human body.

Magnetic field information is often combined with measurements of the temporal and spatial variations in the electrical potentials on the body surface for additional information about the internal condition of the body. Because the magnetic and electric measurements generate a tremendous amount of data in a short period of time, it is desirable to reduce the data and present it in a form which is more familiar and useful to medical diagnosticians. To accomplish this, it is generally believed that a presentation of the sources which generate the measured fields and potentials is desirable. Therefore a procedure which computes the locations and conditions of the sources from the measured data is required.

The problem with computing source locations and conditions from the magnetic field and electric potential measurements, is that the measured information is insufficient to uniquely determine the sources. In other words, many different source distributions can give rise to a specific set of measurements. The difficulty created by this ambiguity is referred to as "the inverse problem". Therefore it is necessary to incorporate as much a-priori knowledge as possible into the calculation.

In addition to an accurate description of the source distribution, it is necessary to be able to show the spatial relationship between the current distribution and anatomical structures in the subject. While techniques for "data fusion" have been developed, there remain many problems with merging complex 3D data sets.

SUMMARY OF INVENTION

In accordance with the present invention a method is provided for locating a current source distribution in a living creature. Sensors, suitable for detecting a magnetic field emanating from the living creature, are placed in various locations outside of the living creature. The living creature is modeled as a collection of adjoining cubic or rectangular regions. Certain of these regions or "voxels" are selected (or segmented) manually using interactive graphical techniques or automatically by choosing a range of parameter values from the magnetic resonance (MR) data. Once the segmentation is complete, a "minimum norm" calculation is performed using the sensor readings and the segmented voxel location information. A current source distribution is determined as a result of these calculations and is displayed along with the anatomical data using volume visualization techniques.

BRIEF DESCRIPTION OF THE DRAWING

While the novel features of the invention are set forth with particularity in the appended claims, the invention, both as to organization and content, will be better understood and appreciated, along with other objects and features thereof, from the following detailed description taken in conjunction with the drawings, in which:

The sole figure, is a flowchart representation of the present inventive method.

DETAILED DESCRIPTION OF THE INVENTION

The present inventive method for computing source distributions uses the minimum norm technique in a modified way so that instead of computing a response matrix for the entire volume of a patient, the response matrix is computed only for locations where sources are expected. In order to do this, the present method takes as input a database of 3-dimensional (3D) anatomical data such as generated using the method described in commonly assigned U.S. Pat. No. 4,729,098 which is incorporated herein by reference. The polygonal mesh generated thereby can be simplified to make the present invention more efficiently practiced using a method such as that described in commonly assigned co-pending application Ser. No. 07/815,772, which is incorporated herein by reference.

The sole FIGURE is a flowchart representation of the present invention. The process begins at function block 110 where an MR or CT scan is performed on a subject, resulting in 3D anatomical data file 112 of the subject in the form of N voxels. At 114, a segmentation of the 3D data is done to reduce data file 112 to data file 116 containing M voxels selected from the N voxels of file 112. At 118, S sensor locations are specified and measurements of magnetic field are taken. At 120, a sequence of single-dipole, forward calculations are performed by placing a dipole at each of the M tissue voxels and for each of 3 orthogonal directions. Therefore a total of 3M distinct sets of forward calculations are used. For each single dipole, the calculated responses at each sensor forms an S-dimensional vector. By grouping the vectors, a 3M×S dimensional matrix 122 is created. Next at 124, a singular value decomposition is performed on this matrix. The eigenvectors whose eigenvalues are above a preselected threshold are retained as "basis vectors". The remaining eigenvectors are discarded. The basis vector(s) 126 can be interpreted as a weighted sum of sources. Therefore each basis vector represents a distributed electromagnetic source. Because the basis vectors are orthogonal and span the measurement space, they can be used to uniquely represent any measurement. At 128, the measurements are expressed over time in terms of basis vectors 126, resulting in a distributed sum of sources which evolves over time. Finally, the computed current distribution is displayed with the anatomical data at 130.

As an example of the present invention, for evoked sources in the brain, it is commonly assumed that the signal arises somewhere in the cerebral cortex. Therefore, in this case, only sources in the cortex need to be considered. This portion of the brain can be grossly identified from the difference in proton density between the brain and the neighboring cerebro spinal fluid. Voxels near the cortex can be selected manually using interactive graphical techniques or they can be selected automatically by choosing a certain range of parameter values from the MR data.

The inventive method begins by mathematically dividing the body volume into a collection of adjoining cubic or rectangular regions. Each region or "voxel" is represented by the numeric co-ordinates of its center or one of its corners. In this way the body volume can be represented as a finite list of coordinate numbers. An electrical current distribution in the body volume is represented through another list associated to the coordinate list, where each set of numbers in the associated list describes the average current intensity and direction within each voxel. If the number of voxels is denoted by N, then 3N numbers are needed to completely specify the current distribution, since 3 numbers can uniquely specify the current within each voxel. Stated another way, any current distribution can be completely represented as a vector of length 3N.

To complete the model setup, the positions of the sensors (to detect the magnetic fields and electrical potentials) are fixed with respect to the body. Typically, there are dozens of sensors. The number of sensors will be denoted by S. Without loss of generality, it can be assumed that each sensor measures a scalar component of the field (or potential) at a specific spatial location. Therefore, the measurement at a specific instant in time can be represented by a vector of length S.

The "response function" of the system can be represented by a matrix, such that if the vector specifying the current distribution is multiplied by the matrix, a new vector of length S is formed which gives the numerical value measured by each detector at a given instant of time:

$$(\text{response vector}) = (\text{current vector}) \times [\text{response matrix}] \quad (1)$$

As the current changes in time, the response vector changes in a corresponding way.

The current distribution is a "row" vector and the measured response is a "column" vector. In this case, the response matrix is a $3N \times S$ matrix. The response matrix can be assumed to be static or at least change much more slowly than the currents. Clearly, the physical information, such as the detector characteristics and the source and sensor geometry, is embedded in the response matrix. A description of how the response matrix is obtained will be provided below.

Since the response vector can be computed from the current vector, equation (1) suggests that the current vector can be computed from the measured response by multiplying both sides of the equation by the inverse of the response matrix. Unfortunately, the response matrix has no inverse, partly because the sensor cannot measure linearly independent information within practical ranges of accuracy, and partly because the matrix does not have the same number of rows and columns, which is a necessary condition. The best that is possible, is that a "singular value decomposition" (SVD) can be performed on the response matrix. (A singular value decomposition is a standard mathematical procedure which is described in many linear algebra textbooks.) This will provide a matrix which can be used to uniquely decompose a measured response into a distributed current source, so that:

$$(\text{response vector}) \times [\text{SVD matrix}] = (\text{current vector}')$$

The ' indicates that the computed current vector here may not be equal to the current vector that generated the response, but it is the "simplest" current distribution which can give rise to the response. The simplicity of the current distribution is measured by its length or "norm" and a shorter vector is "simpler" than a longer vector, hence the name "minimum norm" solution. (In this case, the norm is computed from the square root of the sum of the squares of the vector components.)

The construction of the response matrix is now described. The first step is to obtain a procedure for computing the response of the sensors given an arbitrary current dipole. This procedure also contains information about the locations and orientations of the sensors. Though there are many problems in modeling and the so-called "forward problem", in all cases it is possible to derive approximate analytic (mathematical) expressions for the response. Many different types of sensors and their analytic responses have been reported in the literature. The simple analytic expressions are sufficient for the procedure described here.

The second step is to perform a sequence of response calculations for each sensor, by placing a dipole at each of the N tissue voxels and for each of 3 orthogonal directions. Therefore a total of $3N \times S$ distinct responses are computed. These numbers are placed in appropriate rows and columns to form the response matrix, which is used as described above.

During this second stage, however, there exists the opportunity to embed detailed geometric information. Instead of computing the response matrix for the entire volume as in the usual minimum norm procedure, it is only necessary to compute the response matrix for locations where the sources are expected, such as the cortex in the example described earlier. More specifically, in the case of the brain, instead of computing the response for each voxel, only the voxels near the cortex are used to construct the response matrix. This is referred to as "segmenting". The procedure is thus dependent on and partially limited by the accuracy with which anatomical structures are segmented. This in turn depends on specific physiological knowledge. Such structures are identified from a database containing detailed geometric information about a subject's anatomy. The data base is derived from a 3D reconstruction of the subject's tissues. Such a 3D reconstruction may be obtained from MRI, CT, or other techniques that measure mass and chemical distributions. This segmenting algorithm should take into account knowledge of how the tissues respond to the structural measurement techniques such as computer tomography (CT) or magnetic resonance imaging (MRI). Therefore as segmentation techniques improve and as the supporting scientific information increases, it is expected that the utility of the present invention will increase. Fortunately, even a crude segmenting algorithm will allow construction of a database which is useful.

This leads to several advantages over the traditional minimum-norm approach. The procedure is numerically more stable since (by construction) the dimension of the singular space is reduced. The procedure is more efficient since the sizes of the matrices and vectors are reduced. By construction, the relationship between the current distribution and anatomical structures is obtained directly, rather than through a separate "matching" calculation. This avoids many of the practical difficulties in "data fusion". Volume visualization techniques can be used to display the computed current distribution with the anatomical data.

While the present invention has been described with respect to specific embodiments, many modifications, variations, alterations, substitutions, and equivalents will be apparent to those skilled in the art. Accordingly, the invention is to be considered as limited only by the spirit and scope of the appended claims.

What is claimed is:

1. A method for estimating and displaying a current source distribution in a living creature comprising the steps of:

performing an MR scan of said living creature to obtain 3D anatomical data;

segmenting said data into a quantity M, of tissue voxels;

placing sensors at a quantity S, of locations with respect to said living creature for the purpose of obtaining magnetic field data;

performing a sequence of single-dipole forward calculations on said segmented data to obtain a 3MxS matrix of calculated responses;

computing a singular value decomposition on said matrix whereby a set of basis vectors representing a weighted sum of current sources is obtained;

expressing said basis vectors as distributed current sources data over time; and displaying, using volume visualization techniques, said distributed sources data with said 3D anatomical data.

2. The method of claim 1 wherein said segmenting step is performed manually using interactive graphical techniques.

3. The method of claim 1 wherein said segmenting step is performed automatically by choosing a range of parameter value from the MR data resulting from said MR scanning step.

* * * * *